US012674729B2

(12) United States Patent
Earley et al.

(10) Patent No.: US 12,674,729 B2
(45) Date of Patent: Jul. 7, 2026

(54) WATER VACUUM SAMPLING SYSTEM (WRASSE)

(71) Applicant: The United States of America, as represented by the Secretary of the Navy, Arlington, VA (US)

(72) Inventors: Patrick John Earley, San Diego, CA (US); Brandon Lawson Swope, San Diego, CA (US); Ignacio Rivera-Duarte, San Diego, CA (US); Chandler Petrovich Flynn, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 261 days.

(21) Appl. No.: 18/754,266

(22) Filed: Jun. 26, 2024

(65) Prior Publication Data

US 2026/0002846 A1     Jan. 1, 2026

(51) Int. Cl.
G01N 1/14          (2006.01)
A47L 7/00          (2006.01)
(Continued)

(52) U.S. Cl.
CPC .............. G01N 1/14 (2013.01); A47L 7/0014 (2013.01); G01N 33/18 (2013.01);
(Continued)

(58) Field of Classification Search
CPC .. G01N 1/14; G01N 33/18; G01N 2001/1025; G01N 2001/2071; A47L 7/0014; Y10S 55/03
See application file for complete search history.

(56) References Cited

U.S. PATENT DOCUMENTS 4,246,676 A     1/1981   Hallsworth et al.
4,341,540 A     7/1982   Howerin
(Continued)

FOREIGN PATENT DOCUMENTS

NL     1024424 C2 *   6/2004   ........... A47L 9/1666
RU     2636340 C2 *  11/2017   ............... C21B 7/22

OTHER PUBLICATIONS

NL-1024424-C2, English Translation (Year: 2004).*
RU-2636340-C2, English Translation (Year: 2017).*
NESDIAnnualReport2024.pdf (Year: 2025).*

*Primary Examiner* — Ryan D Walsh
(74) *Attorney, Agent, or Firm* — Naval Information Warfare Center Pacific; Kyle Eppele; J. Eric Anderson

(57)          ABSTRACT

A water vacuum sampling system comprising: an outer housing having a sampling port and a vacuum port, wherein the sampling port is configured to connect to a suction head and the vacuum port is configured to connect to an inlet hose of a vacuum; a velocity dampener cone disposed within the outer housing and configured to receive incoming water, air, and particles that have passed through the sampling port after being sucked up through the suction head, wherein the velocity dampener cone is perforated by a plurality of holes and flares away from the sampling port; a catch basin mounted within the outer housing and having an open upper end and a bottom outlet, wherein the velocity dampener cone extends into the open upper end; and a sample collection container removably attached to the bottom outlet.

20 Claims, 6 Drawing Sheets

(51) Int. Cl.
    *G01N 1/10*              (2006.01)
    *G01N 1/20*              (2006.01)
    *G01N 33/18*            (2006.01)

(52) U.S. Cl.
    CPC ................ *G01N 2001/1025* (2013.01); *G01N 2001/2071* (2013.01); *Y10S 55/03* (2013.01)

(56) References Cited

U.S. PATENT DOCUMENTS

| | | | | |
|---|---|---|---|---|
| 4,360,428 A * | 11/1982 | Comparetto | ......... | A61C 17/065 |
| | | | | 210/512.3 |
| 5,090,976 A * | 2/1992 | Dyson | ................... | A47L 9/1418 |
| | | | | 55/459.1 |
| 6,237,186 B1 * | 5/2001 | Griffiths | ................ | A47L 7/0042 |
| | | | | 15/302 |
| 6,513,189 B1 | 2/2003 | Berry | | |
| 6,579,334 B2 * | 6/2003 | Oh | ......................... | A47L 9/1691 |
| | | | | 55/459.1 |
| 6,912,757 B2 | 7/2005 | Kaufman et al. | | |
| 2002/0020154 A1 * | 2/2002 | Yang | .................... | A47L 9/1666 |
| | | | | 55/428 |
| 2006/0137309 A1 * | 6/2006 | Jeong | .................... | A47L 9/1641 |
| | | | | 55/337 |
| 2012/0311811 A1 * | 12/2012 | Hollis | ....................... | B08B 5/04 |
| | | | | 15/347 |

* cited by examiner

*70*

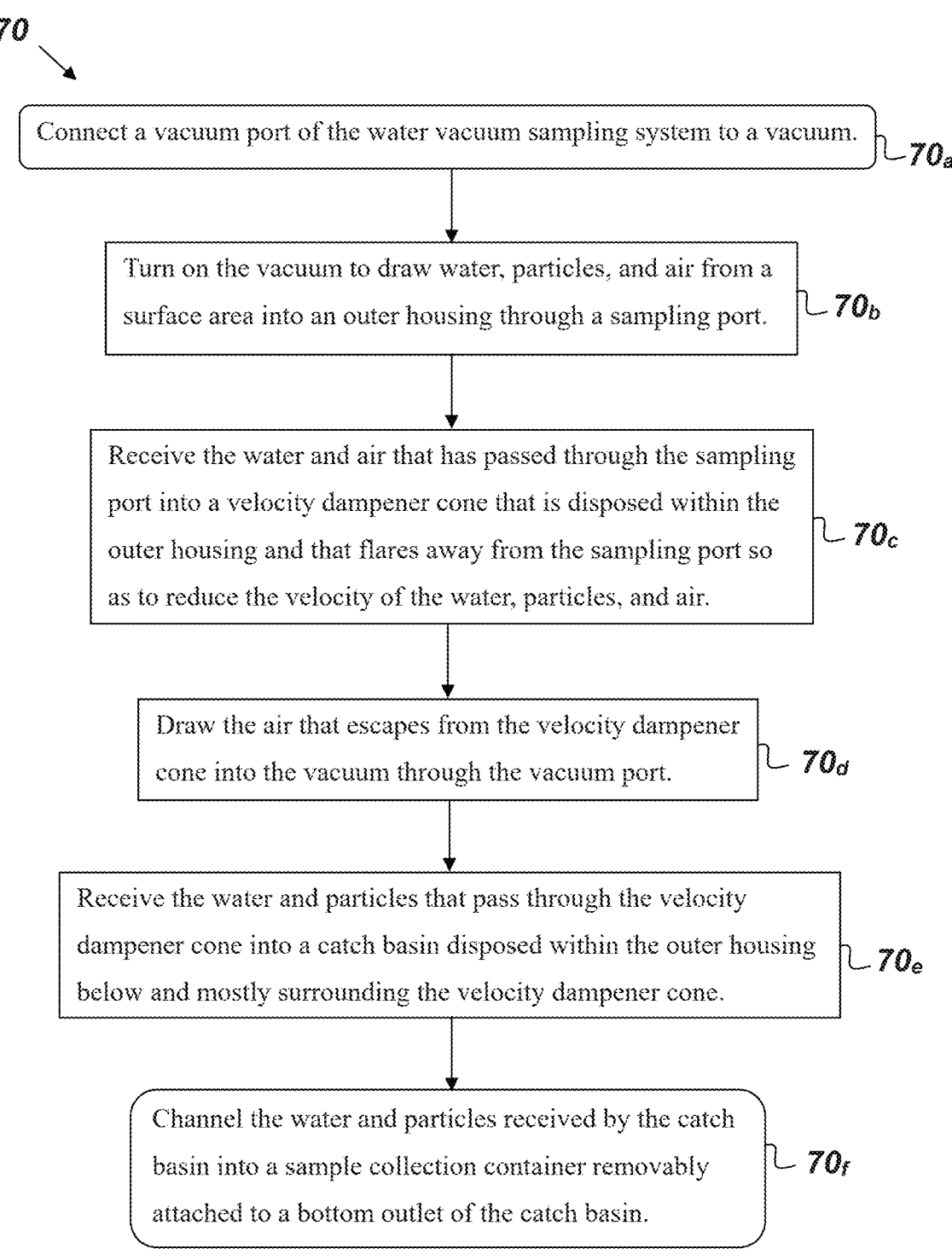

Connect a vacuum port of the water vacuum sampling system to a vacuum. — *70a*

Turn on the vacuum to draw water, particles, and air from a surface area into an outer housing through a sampling port. — *70b*

Receive the water and air that has passed through the sampling port into a velocity dampener cone that is disposed within the outer housing and that flares away from the sampling port so as to reduce the velocity of the water, particles, and air. — *70c*

Draw the air that escapes from the velocity dampener cone into the vacuum through the vacuum port. — *70d*

Receive the water and particles that pass through the velocity dampener cone into a catch basin disposed within the outer housing below and mostly surrounding the velocity dampener cone. — *70e*

Channel the water and particles received by the catch basin into a sample collection container removably attached to a bottom outlet of the catch basin. — *70f*

*Fig. 5*

WATER VACUUM SAMPLING SYSTEM (WRASSE)

FEDERALLY-SPONSORED RESEARCH AND DEVELOPMENT

The United States Government has ownership rights in the invention claimed herein. Licensing and technical inquiries may be directed to the Office of Research and Technical Applications, Naval Information Warfare Center Pacific, Code 72110, San Diego, CA, 92152; voice (619) 553-5118; NIWC_Pacific_T2@us.navy.mil. Reference Navy Case Number 211729.

BACKGROUND OF THE INVENTION

Removal of low, dispersed volumes of water over horizontal surfaces (e.g., puddles) has been achieved in the past with wet-dry vacuums, sponges and other absorbent materials. These existing methods are focused on the removal/cleanup of the water and not on the understanding of any particulate or dissolved contaminants contained within the water itself and do not preserve the integrity of the individual sample without loss or exposure to contaminants or particles that are not exclusively associated with the individual sampling event. There is a need for an improved sample collection device and method.

SUMMARY

Disclosed herein is a water vacuum sampling system comprising an outer housing, a velocity dampener cone, a catch basin, and a sample collection container. The outer housing has a sampling port and a vacuum port. The sampling port is configured to connect to a suction head and the vacuum port is configured to connect to an inlet hose of a vacuum. The velocity dampener cone is disposed within the outer housing and is configured to receive incoming water, air, and particles that have passed through the sampling port after being sucked up through the suction head. The velocity dampener cone is perforated by a plurality of holes and flares away from the sampling port. The catch basin is mounted within the outer housing and has an open upper end and a bottom outlet. The velocity dampener cone extends into the open upper end, and the sample collection container is removably attached to the bottom outlet.

Also disclosed herein is a method for using a water vacuum sampling system comprising the following steps. A first step provides for connecting a vacuum port of the water vacuum sampling system to a vacuum. Another step provides for turning on the vacuum to draw water, particles, and air from a surface area into an outer housing through a sampling port. Another step provides for receiving the water and air that has passed through the sampling port into a velocity dampener cone that is disposed within the outer housing and that flares away from the sampling port so as to reduce the velocity of the water, particles, and air. The velocity dampener cone is perforated to allow the air to escape through the perforations and through a bottom of the velocity dampener cone. Another step provides for drawing the air that escapes from the velocity dampener cone into the vacuum through the vacuum port. Another step provides for receiving the water and particles that pass through the velocity dampener cone into a catch basin disposed within the outer housing below and mostly surrounding the velocity dampener cone. Another step provides for channeling the water and particles received by the catch basin into a sample collection container removably attached to a bottom outlet of the catch basin.

BRIEF DESCRIPTION OF THE DRAWINGS

Throughout the several views, like elements are referenced using like references. The elements in the figures are not drawn to scale and some dimensions are exaggerated for clarity.

FIG. 5 is a flowchart of a method for using a water vacuum sampling system.

DETAILED DESCRIPTION OF EMBODIMENTS

The disclosed methods and systems below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

References in the present disclosure to "one embodiment," "an embodiment," or any variation thereof, means that a particular element, feature, structure, or characteristic described in connection with the embodiments is included in at least one embodiment. The appearances of the phrases "in one embodiment," "in some embodiments," and "in other embodiments" in various places in the present disclosure are not necessarily all referring to the same embodiment or the same set of embodiments.

As used herein, the terms "comprises," "comprising," "includes," "including," "has," "having," or any variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

Additionally, use of words such as "the," "a," or "an" are employed to describe elements and components of the embodiments herein; this is done merely for grammatical reasons and to conform to idiomatic English. This detailed description should be read to include one or at least one, and the singular also includes the plural unless it is clearly indicated otherwise.

Figure 1:
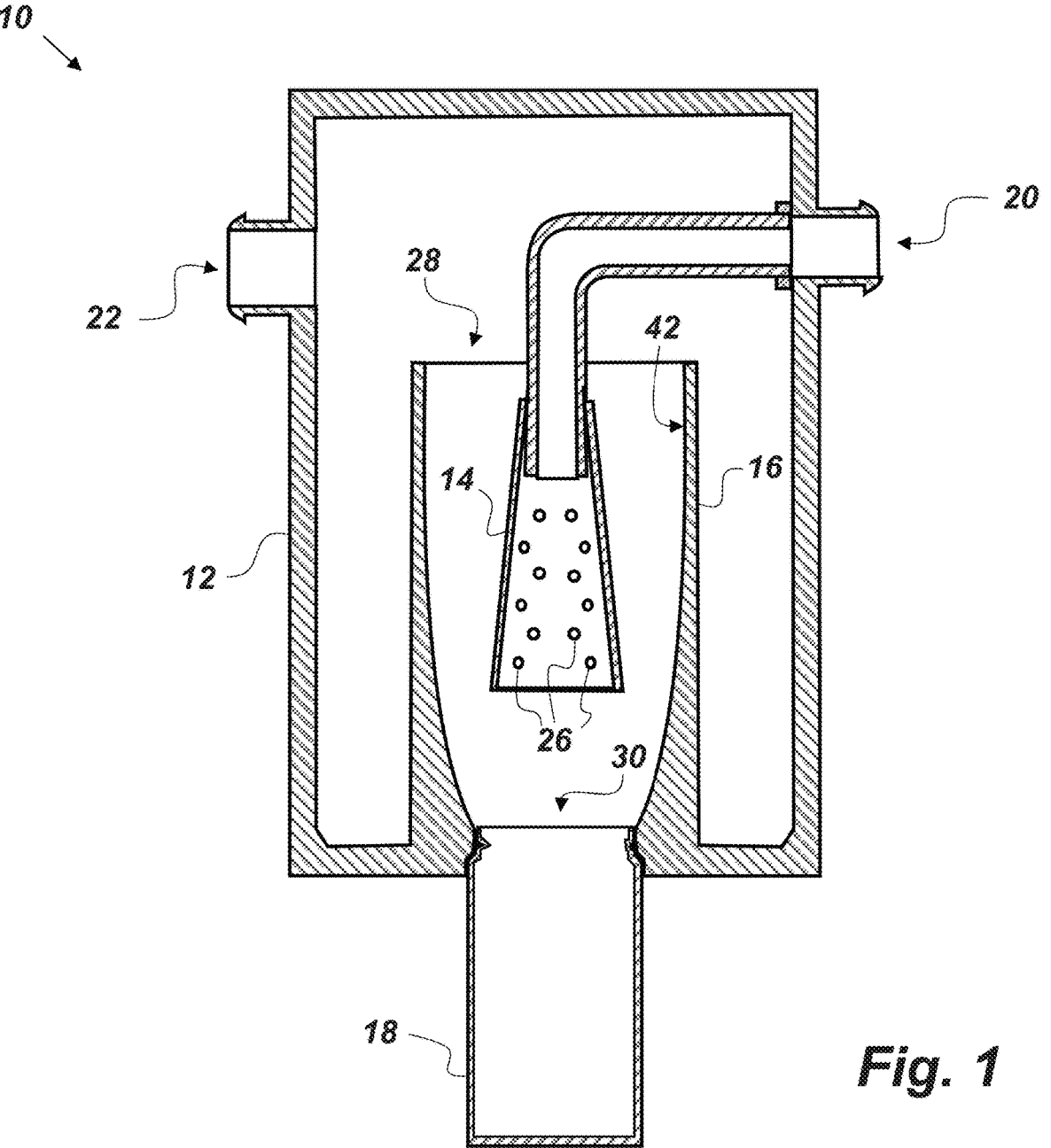
FIG. 1 is a cross-sectional, side-view illustration of an embodiment of a water vacuum sampling system.
Figure 2:
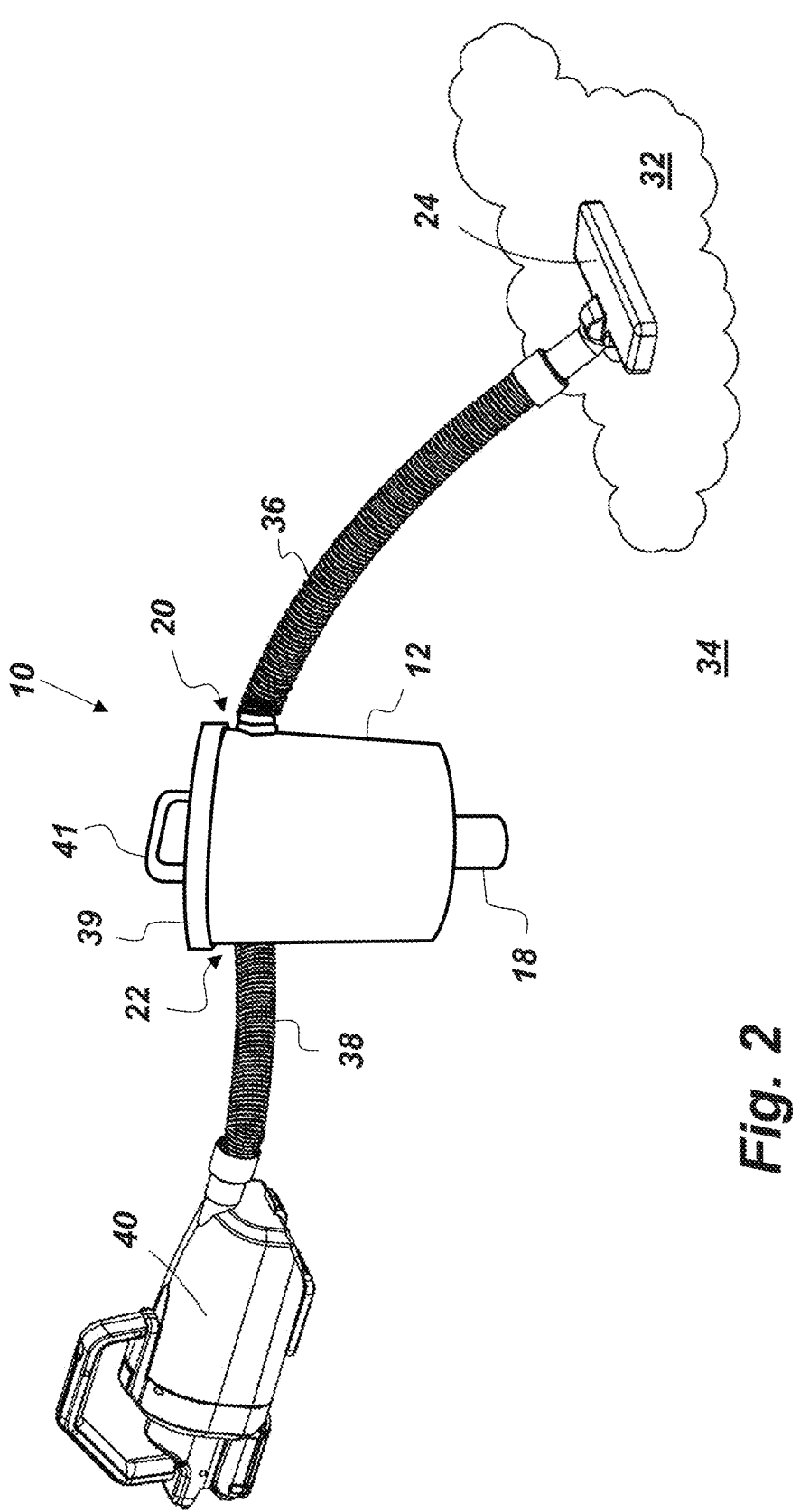
FIG. 2 is a perspective-view illustration of an embodiment of a water vacuum sampling system.

FIG. 1 is a cross-sectional, side-view illustration of a water vacuum sampling system 10 (hereinafter referred to as WRASSE 10) that comprises, consists of, or consists essentially of and outer housing 12, a velocity dampener cone 14, a catch basin 16, and a sample collection container 18. The outer housing 12 has a sampling port 20 and a vacuum port 22. The velocity dampener cone 14 is disposed within the outer housing 12 and configured to receive incoming water, air, and particles that have passed through the sampling port 22 after being sucked up through a suction head 24 (as shown in FIG. 2). The velocity dampener cone 14 is perforated by a plurality of holes 26 and flares away from the sampling port 22. The holes 26 may be staggered. The catch basin 16 is mounted within the outer housing 12 and has an open upper end 28 and a bottom outlet 30. The velocity dampener cone 14 extends into the open upper end 28. The sample collection container 18 is removably attached to the bottom outlet 30. In the embodiment of the WRASSE 10 shown in FIG. 1, the open upper end 28 is higher than any part of the velocity dampener cone 14 such that the velocity dampener cone 14 is completely disposed within the catch basin 16. Also in the embodiment of the WRASSE 10 shown in FIG. 1, the sample collection container 18 is screwed to the bottom outlet 30.

FIG. 2 is a perspective-view illustration of an embodiment of the WRASSE 10 showing how the WRASSE 10 may be used to collect samples of a puddle 32 (i.e., water and sediment/particulates that have collected on a surface 34). The velocity damper cone 14 allows for a vacuum-applied airflow to draw a mixture of air, water and suspended particulates into the WRASSE 10, to separate out the water and suspended particulates as a sample, and to deposit the sample into the interchangeable sample collection container 18. In the embodiment shown in FIG. 2, the sampling port 20 is connected to the suction head 24 via a flexible hose 36, and the vacuum port 22 is connected to an inlet hose 38 of a vacuum 40. The embodiment of the WRASSE 10 shown in FIG. 2 further comprises a lid 39 and a handle 41.

The outer housing 12 may be made of material capable of maintaining an internal negative pressure of at least 15,000 pascals. Suitable examples of material from which the outer housing 12 may be made include, but are not limited to, plastic, wood, glass, and metal. The catch basin 16 ideally should have a tapered inner surface 42 (See FIG. 1) to channel water and particulates into the sample collection container 18. The catch basin 16 may be integrated into the outer housing 12 such as is shown in FIG. 1 or it can be a separate component that is attached to the outer housing 12. The WRASSE 10 may be manufactured by any means known to those having ordinary skill in the art. For example, the outer housing 12 and the catch basin 16 may be manufactured with additive manufacturing processes such as three-dimensional printing.

Figure 3:
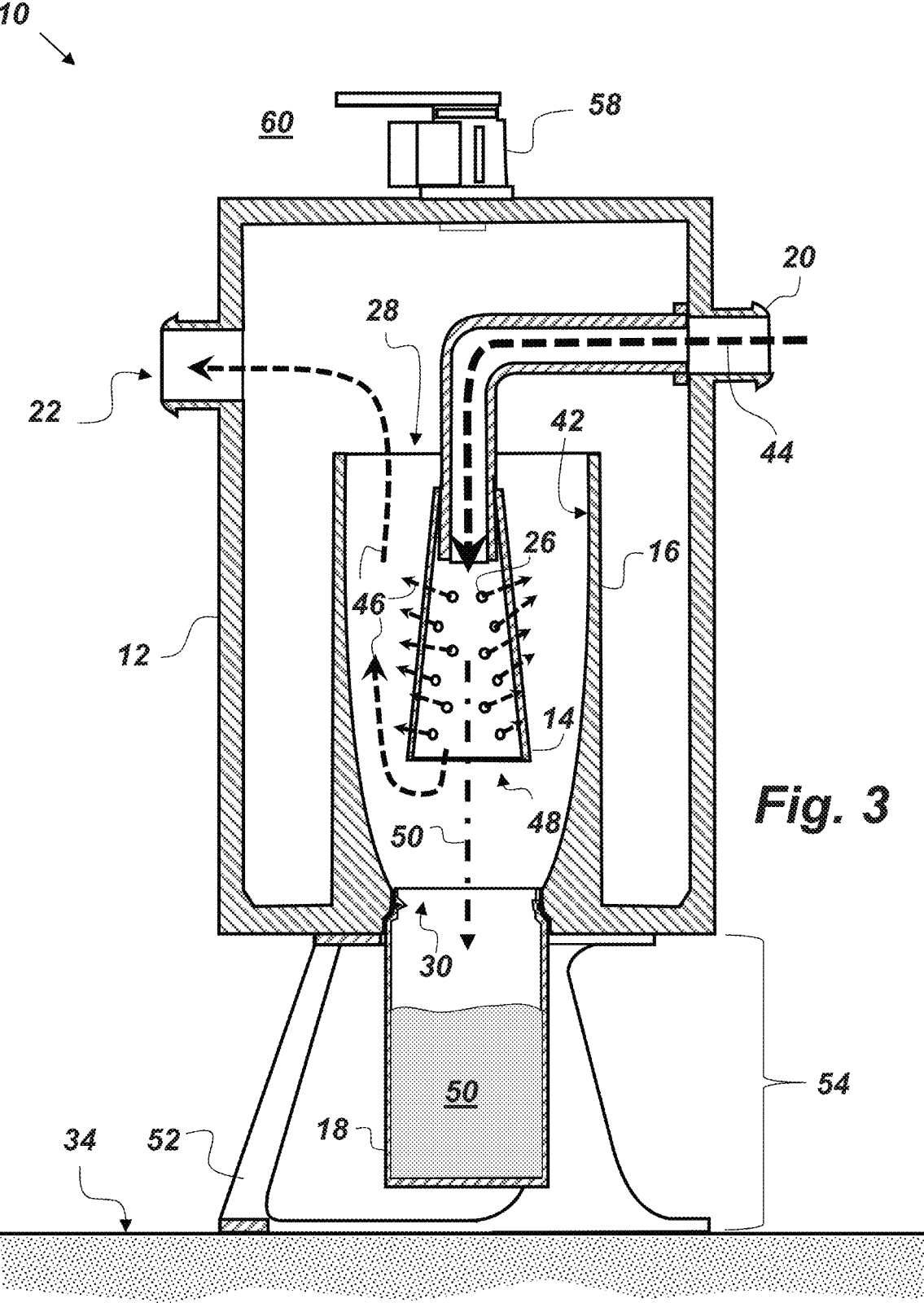
FIG. 3 is a cross-sectional, side-view illustration of an embodiment of a water vacuum sampling system.

FIG. 3 is a cross-sectional, side-view of an embodiment of the WRASSE 10 showing a mixture 44 of air, water, and particulates/sediment being drawn into the velocity dampener cone 14 through the sampling port 20. Once inside the velocity dampener cone 14, the velocity of the mixture 44 is reduced and air 46 from the mixture 44 is able to escape out the holes 26 and out a bottom 48 of the velocity dampener cone 14. The velocity dampener cone 14 is ideally placed completely inside the catch basin 16 such that bottom 48 and the holes 26 are disposed below the open upper end 28 of the catch basin 16. The bottom 48 is aligned with the bottom outlet 30 to allow gravity to pull a water and particulate sample 50 that was part of the mixture 44 to drop into the sample collection container 18. The purpose of the velocity dampener cone 14 is to increase chaotic airflow and reduce the velocity of the mixture 44 of air, water, and particulates/ sediment to help the sample 50 drop out of the mixture 44. After the air 46 has escaped the velocity dampener cone 14, it is sucked out the vacuum port 22. The WRASSE 10 is configured such that water and sediment/particulates that escape with the air 46 out of the velocity dampener cone 14 impinge on the inner walls 42 of the catch basin 16 to be channeled into the bottom outlet 30.

Figure 4:
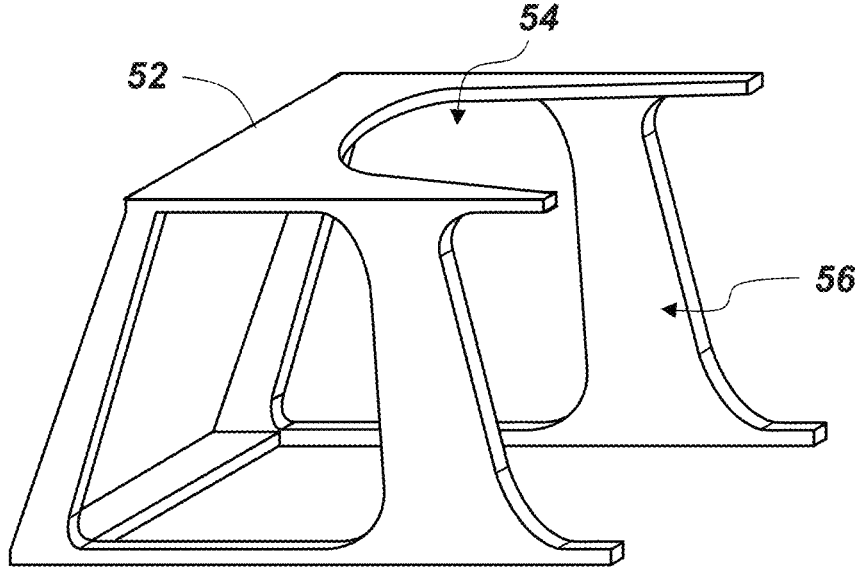
FIG. 4 is a perspective-view illustration of a stand for an embodiment of a water vacuum sampling system.

FIG. 4 is a perspective view of a stand 52, which is also illustrated in the embodiment of the WRASSE 10 shown in FIG. 3. The stand 52 is configured to support the outer housing 12 above the surface 34. The stand 52 includes a top opening 54 aligned with the bottom outlet 30 and a side opening 56 designed such that when the housing 12 is resting on the stand 52, the sample collection container 18 is disposed within the top opening 54 and is accessible from the side opening 56 by an operator's hand without having to move the outer housing 12 such that the sample collection container 18 is capable of being swapped out with the outer housing 18 resting on the stand 52.

Returning to FIG. 3, that embodiment of the WRASSE 20 further comprises an airflow regulator 58 connected to the outer housing 12 and configured to adjust a level of suction at the suction head 24. In this embodiment, the airflow regulator 58 is a hand-operated air valve mounted to the outer housing 12 and disposed to allow external air 60 into the outer housing 12. The velocity dampener cone 14 and the catch basin 16 may be shaped and disposed with respect to each other so as to maximize fluid and particulate capture in the catch basin 16 so as to minimize water and particle loss. The sample collection container 18 may be screwed to the bottom outlet 30.

FIG. 5 is a flowchart of a method 70 for using a water vacuum sampling system comprising the following steps. One step 70a provides for connecting a vacuum port of the water vacuum sampling system to a vacuum. Another step 70b provides for turning on the vacuum to draw water, particles, and air from a surface area into an outer housing through a sampling port. Another step 70c provides for receiving the water and air that has passed through the sampling port into a velocity dampener cone that is disposed within the outer housing and that flares away from the sampling port so as to reduce the velocity of the water, particles, and air. The velocity dampener cone is perforated to allow the air to escape through the perforations and through a bottom of the velocity dampener cone. Another step 70a provides for drawing the air that escapes from the velocity dampener cone into the vacuum through the vacuum port. Another step 70e provides for receiving the water and particles that pass through the velocity dampener cone into a catch basin disposed within the outer housing below and mostly surrounding the velocity dampener cone. Another step 70f provides for channeling the water and particles received by the catch basin into a sample collection container removably attached to a bottom outlet of the catch basin.

The WRASSE 10 and method 70 may be used to establish a uniform approach to collecting/testing samples of water and suspended particulates from any surface area (e.g., surface 34), which may include, but is not limited to, a dock, a road, a factory floor, a food processing facility, etc. A previously-dry surface may be wetted with a predetermined amount of water prior to turning on the vacuum 40. Then, after the surface has been wetted, one may wait a predetermined amount of time before drawing the water, particles, and air from the surface area so as to simulate exposure of the surface area to storm water. Once the sample has been collected, the water and particles in the sample collection container may be tested for contaminants. If additional samples are desired from the same area, once the sample collection container is sufficiently full, it may be removed from the bottom outlet without moving the outer housing 12, and a new/clean sample collection container may be attached to the bottom outlet 30. The swapping of sample collection containers may be done with the vacuum on or off. However, it is preferable to swap sample collection containers with the vacuum off. After retrieving a sample, the WRASSE 10 may be cleaned and used to collect different samples from a different surface area. The airflow regulator 58 may be used to adjust the level of suction so as to minimize splatter outside of the catch basin 16 of the water and particles coming out of the velocity dampener cone 14. The WRASSE 10 can be modified to work with any on-hand commercial or household vacuum cleaner, wet or dry.

Figure 6:
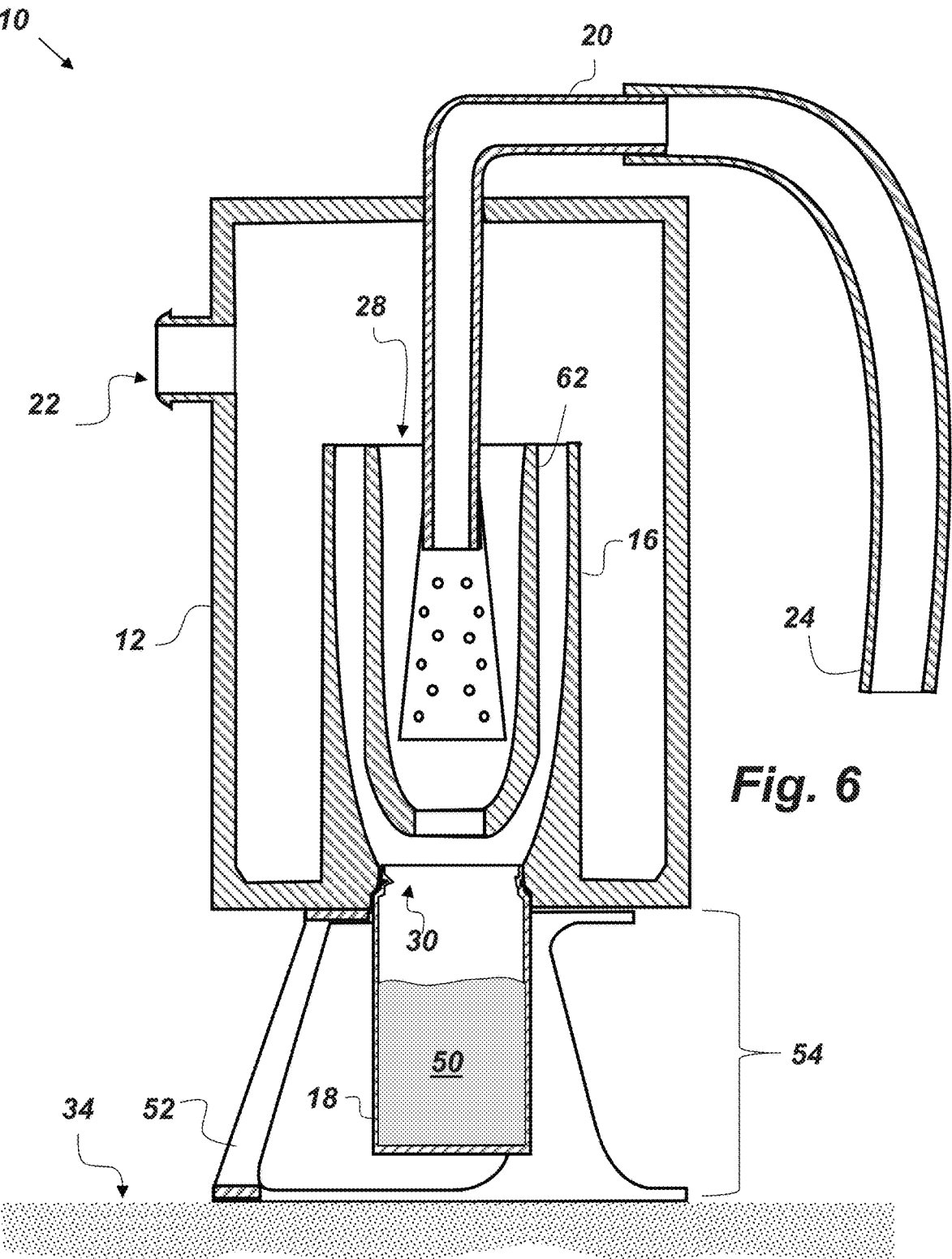
FIG. 6 is a cross-sectional, side-view illustration of an embodiment of a water vacuum sampling system.

FIG. 6 is a cross-sectional, side-view illustration of another embodiment of the WRASSE 10 comprising a second catch basin 62 nested within the catch basin 16. The WRASSE 10 may have any desired number of internal catch basins disposed within the outer housing 12. As mentioned above, the WRASSE 10 may include an airflow regulator 58 attached to the outer housing 12 to control water/air intake, but a commercially available vacuum with suction controls may be used in lieu of the airflow regulator 58. Also shown in FIG. 6, the suction head 24 is a simple flexible hose.

From the above description of the WRASSE 10 and the method 70, it is manifest that various techniques may be used for implementing the concepts thereof without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the WRASSE 10 and method 70 are not limited to the particular embodiments described herein, but are capable of many embodiments without departing from the scope of the claims.

We claim:

1. A water vacuum sampling system comprising:
an outer housing having a sampling port and a vacuum port, wherein the sampling port is configured to connect to a suction head and the vacuum port is configured to connect to an inlet hose of a vacuum;
a velocity dampener cone disposed within the outer housing and configured to receive incoming water, air, and particles that have passed through the sampling port after being sucked up through the suction head, wherein the velocity dampener cone is perforated by a plurality of holes and flares away from the sampling port;
a catch basin mounted within the outer housing and having an open upper end and a bottom outlet, wherein the velocity dampener cone extends into the open upper end; and
a sample collection container removably attached to the bottom outlet.

2. The water vacuum sampling system of claim 1, further comprising a stand configured to support the outer housing above a surface, wherein the stand includes a top opening and a side opening such that when the outer housing is resting on the stand, the sample collection container is received into the top opening and accessible from the side opening such that the sample collection container is capable of being swapped out with the outer housing resting on the stand.

3. The water vacuum sampling system of claim 2, wherein the velocity dampener cone is configured to reduce a velocity of the incoming air, water, and particles and to separate the air from the water and the particles such that the water and particles fall into the catch basin after passing through the velocity dampener cone.

4. The water vacuum sampling system of claim 3, wherein the catch basin has inner walls that taper down from the open upper end to the bottom outlet.

5. The water vacuum sampling system of claim 4, wherein the velocity dampener cone is disposed below the upper open end so as to be disposed completely inside the catch basin.

6. The water vacuum sampling system of claim 5, further comprising an airflow regulator connected to the outer housing and configured to adjust a level of suction at the suction head.

7. The water vacuum sampling system of claim 6, wherein the airflow regulator is an air valve disposed to allow external air into the outer housing.

8. The water vacuum sampling system of claim 7, wherein the velocity dampener cone and the catch basin are shaped and disposed with respect to each other so as to maximize fluid and particulate capture in the catch basin so as to minimize water and particle loss.

9. The water vacuum sampling system of claim 8, wherein the sample collection container is screwed to the bottom outlet.

10. The water vacuum sampling system of claim 9, wherein the outer housing comprises an upper detachable lid on which the airflow regulator is connected.

11. A method for using a water vacuum sampling system comprising:
connecting a vacuum port of the water vacuum sampling system to a vacuum;
turning on the vacuum to draw water, particles, and air from a surface area into an outer housing through a sampling port;
receiving the water and air that has passed through the sampling port into a velocity dampener cone that is disposed within the outer housing and that flares away from the sampling port so as to reduce the velocity of the water, particles, and air, wherein the velocity dampener cone is perforated to allow the air to escape through the perforations and through a bottom of the velocity dampener cone;
drawing the air that escapes from the velocity dampener cone into the vacuum through the vacuum port;
receiving the water and particles that pass through the velocity dampener cone into a catch basin disposed within the outer housing below and mostly surrounding the velocity dampener cone; and
channeling the water and particles received by the catch basin into a sample collection container removably attached to a bottom outlet of the catch basin.

12. The method of claim 11, further comprising wetting the surface area with a predetermined amount of water prior to turning on the vacuum.

13. The method of claim 12 further comprising waiting a predetermined amount of time after the wetting step before drawing the water, particles, and air from the surface area so as to simulate exposure of the surface area to storm water.

14. The method of claim 13, further comprising testing the water and particles in the sample collection container for contaminants.

15. The method of claim 14, further comprising:
replacing the sample collection container with a clean sample collection container;
cleaning the water vacuum sampling system; and
repeating the steps of claim 14 at a different surface area.

16. The method of claim 11, further comprising resting an outer housing of the water vacuum sampling system on a stand configured to support the outer housing above the surface area such that the sample collection container hangs from the bottom outlet within in a top opening in the stand.

17. The method of claim 16, further comprising swapping out the sample collection container through a side opening in the stand after the water and particles have been channeled into the sample collection container without removing the outer housing from the stand.

18. The method of claim 17, further comprising separating the water and particles from the air in the velocity dampener cone such that the water and particles fall into the catch basin after passing through the velocity dampener cone.

19. The method of claim 18, further comprising adjusting a level of suction at the suction head by adjusting an airflow regulator connected to the outer housing to allow external air to enter into the outer housing.

20. The method of claim 19, further comprising adjusting the level of suction so as to minimize splatter outside of the catch basin of the water and particles coming out of the velocity dampener cone.

*    *    *    *    *